(12) United States Patent
Haskel et al.

(10) Patent No.: US 8,084,050 B2
(45) Date of Patent: Dec. 27, 2011

(54) COMPOSITIONS COMPRISING COMBINATIONS OF SENSATES

(75) Inventors: Ariel Haskel, East Brunswick, NJ (US); Subhash Harmalker, Somerset, NJ (US); Jairajh Mattai, Piscataway, NJ (US)

(73) Assignee: Colgate-Palmolive Company, New York, NY (US)

( * ) Notice: Subject to any disclaimer, the term of this patent is extended or adjusted under 35 U.S.C. 154(b) by 1447 days.

(21) Appl. No.: 11/548,586

(22) Filed: Oct. 11, 2006

(65) Prior Publication Data

US 2008/0089850 A1    Apr. 17, 2008

(51) Int. Cl.
*A61K 8/02* (2006.01)

(52) U.S. Cl. ...................................... 424/401

(58) Field of Classification Search .................. None
See application file for complete search history.

(56) References Cited

U.S. PATENT DOCUMENTS

| | | | |
|---|---|---|---|
| 4,438,095 A | 3/1984 | Grollier et al. |
| 4,894,220 A | 1/1990 | Nabi et al. |
| 5,534,265 A | 7/1996 | Fowler et al. |
| 5,602,178 A | 2/1997 | Caroselli et al. |
| 5,656,257 A | 8/1997 | Fealy et al. |
| 5,725,865 A | 3/1998 | Mane |
| 5,843,466 A | 12/1998 | Mane |
| 5,900,394 A | 5/1999 | Goel et al. |
| 6,083,899 A | 7/2000 | Baker et al. |
| 6,267,974 B1 | 7/2001 | Suares et al. |
| 6,379,654 B1 | 4/2002 | Gebreselassie et al. |
| 6,395,690 B1 | 5/2002 | Tsaur |
| 6,533,873 B1 | 3/2003 | Margosiak et al. |
| 6,627,233 B1 | 9/2003 | Wolf et al. |
| 6,669,929 B1 | 12/2003 | Boyd et al. |
| 6,719,966 B2 | 4/2004 | Abrutyn |
| 6,780,443 B1 | 8/2004 | Nakatsu et al. |
| 6,805,855 B2 | 10/2004 | Mattai et al. |
| 6,890,567 B2 | 5/2005 | Nakatsu et al. |
| 6,897,195 B2 | 5/2005 | Su et al. |
| 6,899,901 B2 | 5/2005 | Nakatsu et al. |
| 7,067,152 B2 | 6/2006 | Shefer |
| 2002/0119110 A1 | 8/2002 | Mahe et al. |
| 2004/0082654 A1 | 4/2004 | Pesce et al. |
| 2005/0004274 A1 | 1/2005 | Healy et al. |
| 2005/0129721 A1 | 6/2005 | Ishida et al. |
| 2005/0142095 A1 * | 6/2005 | Scancarella et al. ............ 424/74 |
| 2005/0192189 A1 * | 9/2005 | Wagner et al. ................ 510/130 |
| 2006/0067961 A1 | 3/2006 | Krzysik et al. |
| 2006/0067962 A1 | 3/2006 | Krzysik et al. |
| 2006/0160713 A1 | 7/2006 | Sekine et al. |
| 2006/0269500 A1 | 11/2006 | Riemer et al. |
| 2007/0077331 A1 | 4/2007 | Kiefer et al. |
| 2007/0221236 A1 | 9/2007 | Kiefer et al. |
| 2007/0225378 A1 | 9/2007 | Ishida et al. |
| 2008/0085247 A1 | 4/2008 | Langner et al. |
| 2008/0085290 A1 | 4/2008 | Flugge-Berendes et al. |
| 2008/0112910 A1 | 5/2008 | Ishida et al. |
| 2008/0253973 A1 | 10/2008 | Tamarkin et al. |
| 2008/0267889 A1 | 10/2008 | Cernasov et al. |

FOREIGN PATENT DOCUMENTS

| | | |
|---|---|---|
| DE | 103 09 180 A | 6/2004 |
| EP | 0 211 392 A | 2/1987 |
| EP | 1 197 205 A | 4/2002 |
| EP | 1 529 515 A | 5/2005 |
| JP | 06-329528 | 11/1994 |
| JP | 10-231238 | 9/1998 |
| JP | 2005239633 | 9/2005 |
| RU | 2238715 C1 | 10/2004 |
| WO | WO 99/39683 A | 8/1999 |
| WO | WO 00/42983 | 7/2000 |
| WO | WO 2004112735 A1 * | 12/2004 |

OTHER PUBLICATIONS

Definition of humectant from freedictionary.com, accessed Jun. 29, 2011.*
EPO Document No. XP-002463427, Abstract for JP 2005239633, Sep. 8, 2005.
International Search Report, for PCT/US2007/079480 mailed Feb. 15, 2008.
C.O. Bigelow Raspberry Mentha Body Wash. Sale in U.S. Circa Dec. 2008.
C.O. Bigelow Orange Mentha Body Wash. Sale in U.S. Circa Dec. 2008.
C.O. Bigelow Mentha Body Wash. Sale in U.S. Circa Aug. 2007.
C.O. Bigelow Mentha body Lotion. Sale in U.S. Circa Aug. 2007.
Office Action from Corresponding Russian patent application (RU2009117450) mailed on Jul. 2, 2010.

* cited by examiner

*Primary Examiner* — Nissa Westerberg
(74) *Attorney, Agent, or Firm* — Michael F. Morgan

(57) ABSTRACT

Compositions comprising a first sensate, a second sensate, and a cationic polymeric compound are described, as well as methods for using such compositions in oral care and personal care applications.

18 Claims, No Drawings

US 8,084,050 B2

COMPOSITIONS COMPRISING COMBINATIONS OF SENSATES

BACKGROUND OF THE INVENTION

Sensates have been used in a wide range of consumer applications. For example, menthol is a well known sensate that is known for its immediate, sharp cooling effect, as well as its potential irritation and burning sensation when applied to skin. The addition of menthyl lactate (the lactate ester of menthol) to a personal care formulation containing menthol may partially offset these undesirable effects, providing a milder and more pleasant sensation.

Efforts are ongoing to formulate mild and non-irritating combinations of sensates in consumer products. While many sensates provide a cooling, tingling or refreshing sensation when incorporated into consumer products, some combinations may be too harsh for certain users, including those having high levels of sensitivity, e.g., children or adults with sensitive skin and/or mucous membranes. On the other hand, when the amounts of sensate materials, either alone or in combination, are sufficiently reduced in an effort to eliminate irritation, the beneficial and desirable cooling, tingling or refreshing sensations may be lost.

Accordingly, there is an ongoing need for personal care and oral care products comprising sensates that are able to provide beneficial and perceptible cooling, tingling or refreshing effects to the body, wherein said effects are mild and non-irritating for sensitive users, but still noticeable, pleasant and long-lasting.

BRIEF SUMMARY OF THE INVENTION

It has been discovered that compositions comprising optimal ratios of two or more sensates, coupled with the addition of a cationic polymeric compound and, optionally, a solubilizer, results in compounds that are beneficial in that they are mild, but still retain the long lasting cooling, tingling and refreshing benefits desired when applied to the body.

The present invention is directed, in certain embodiments, to compositions comprising a first sensate, a second sensate and a cationic polymeric compound, and optionally a solubilizer.

The present invention is directed, in other embodiments, to methods for providing a cooling, tingling or refreshing sensation to the body, comprising application of a composition comprising a first sensate, a second sensate and a cationic polymeric compound to the body. In various embodiments, the methods described herein further provide the step of removing the composition from contact with the body.

The present invention is directed, in other embodiments, to methods for prolonging a cooling, tingling or refreshing sensation to the body, said method comprising the step of applying a composition to the body.

The present invention is directed, in other embodiments, to methods for signaling the delivery of an active agent to a body, comprising application of a composition comprising a first sensate, a second sensate, a cationic polymeric compound and an active agent to the body.

DETAILED DESCRIPTION OF THE INVENTION

As used throughout, ranges are a shorthand for describing each and every value that is within the range. Any value within the range can be selected as the terminus of the range. In addition, all references cited in the present disclosure are hereby incorporated by reference in their entireties. If any conflicts exist between definitions in the present disclosure from those in any cited references, those of the present disclosure take precedence.

As used herein, the term "sensate" refers to a compound that provides a cooling, tingling or refreshing sensation, either through the endothermic process of physical lowering of temperature; or through the physiological cooling process associated with, e.g., cold menthol receptor (TRPM8), or any other receptors generally located at or near nerve endings. Sensates that are useful for the present invention include, e.g., menthol, as well as menthol derivates such as menthol with a carboxamide derivative, cyclohexanecarboxamide, dimethyl menthyl succinimide, menthyl lactate (available under the trade name Frescolat ML from Symrise GmbH & Co., Holzminden, Germany), menthone glycerin acetal (available under the trade name Frescolat MGA from Symrise GmbH & Co., Holzminden, Germany), menthoxypropanediol (commercially available under the trade name Coolact 10 and Coolact P (−)-isopulegol from Takasago Int'l Corp., Tokyo, Japan); neoisomenthol, neomenthol, isomenthol, PMD 38 p-menthane-3,8,-diol, (2R)-3-(1-menthoxy)propane-1,2-diol, (2RS)-3-(1-menthoxy)propane-1,2-diol; N-ethyl-pmenthane-3-carboxamide (WS-3), ethyleneglycol p-menthane-3-carboxylate (WS-4), ethyl 3-(p-menthane-3-carboxamido)acetate (WS-5), N-(4-methoxyphenyl)-p-menthane-3-carboxamide (WS-12), N-t-butyl-p-menthane-carboxamide (WS-14),2-isopropyl-N-2,3-trimethylbutyramide (WS-23), 1-glyceryl p-menthane-3-carboxylate (WS-30) (all commercially available from Millennium Chemicals, Hunt Valley, Md., USA); non-menthol derivatives such as phenol derivatives, e.g., thymol and eugenol, Icilin (Phoenix Pharmaceuticals, Belmont, Calif., USA), 2(5H)-NIPF (Nestec, Vevey, Switzerland), 4-methyl-3-(1-pyrrolidinyl)2[5H]-furanone, MPD vanillyl acetal (Takasago Int'l Corp., Tokyo, Japan) Hotact VBE (Lipo Chemicals, Inc., Paterson, N.J., USA), or capsaicin (derivative of cayenne pepper). However, any compositions not listed here but having the characteristics of sensates as defined herein may be useful for the present embodiments.

Sensates have wide application for their analgesic, anesthetic, freshening or flavoring and related effects. For example, menthol and menthol derivates have been used widely in foods, beverages, oral care, personal care and pharmaceutical products, such as lip balms and cough and throat medicines for relief of pain associated with the oral cavity. Sensates have also been used widely in combination products used for relief of muscle aches, sprains, and similar conditions, as well as decongestants. Sensates are major ingredients in certain medications for treatment of sunburns, as well as personal care products such as bath products and shampoos.

However, it has been reported that even small amounts of sensates potentially have a strong and excessively irritating effect on certain users. In embodiments of the present invention, the amounts of the first sensate are generally kept below about 1.0%, e.g., about 0.01 to about 0.3% in certain embodiments, and about 0.05 to 0.25% in other embodiments. Similarly, the amounts of the second sensate are about 0.01 to about 0.45% in certain embodiments, and about 0.05 to about 0.4% in other embodiments. Additionally, it has been found that ratio of the first sensate to the second sensate of about 1:1 to about 1:2.5 is particularly desirable in certain embodiments. In exemplary embodiments, the ratio of the first sensate to the second sensate is about 1:1, 1:1.5, 1:2 and 1:2.5.

It has been found that the combination of two or more sensates often has advantageous effects. For example, the addition of menthyl lactate to a composition containing menthol may somewhat offset the irritating effect of menthol alone, thus lessening the harshness of such compositions for personal care applications such as bath, shower and hair products. Discussions of the benefits and uses of menthyl lactate can be found throughout the art, e.g., U.S. Patent Application No. 2004/0082654 A1 to Pesce et al. Additionally, the beneficial effects of the menthol/menthyl lactate combination have been discussed in, e.g., U.S. Pat. No. 5,602,178 to Caroselli et al. and U.S. Pat. No. 6,897,195 to Su et al.

However, combinations of sensates may not always completely remove the irritating effects, particularly when used by subjects having sensitive skin, oral cavities or mucous membranes. Personal preference may vary widely on the amount of cooling, tingling or refreshing that is desired in compositions comprising sensates either alone or in combination with other sensates. Furthermore, personal care compositions (such as bodywashes) containing sensates that are currently known in the art are not always capable of providing a long-lasting effect; i.e., their cooling, tingling or refreshing effect is immediately lost when the compositions are rinsed off the body.

In certain embodiments, the compounds comprise a cationic polymeric compound. As used herein, the term "cationic polymeric compound" refers to a cationic polysaccharide or polysaccharide derivative that enhances the conditioning performance of the present compositions, and also serves as a delivery system for the other ingredients. Exemplary cationic polymeric compounds may include, but are not limited to: cationic cellulosic polymers and derivatives thereof (for example, polysaccharide derivatives of methyl, ethyl, hydroxypropyl, hydroxyethyl, carboxymethyl and carboxymethylhydroxypropyl cellulose, e.g., trimethylammonium hydroxyethylcellulose), guar gums (for example, cationic or quaternized derivatives of hydroxypropyl, hydroxyethyl, sodium carboxymethyl and carboxymethylhydroxypropyl guar gums, e.g., guar hydroxypropyltrimonium chloride), Quaternium-19, -23, -40, -57, poly (dimethyldiallylammonium chloride), poly(dimethyl butenyl ammonium chloride)-, w-bis (dipropyldiallylammonium chloride), poly(dipropyldiallylammonium chloride), poly(diallylpiperidinium chloride), poly(vinyl pyridinium chloride), quaternized poly(vinyl alchohol), quaternized poly(dimethylaminoethylmethacrylate) and mixtures thereof.

Additionally, when compounds such as xantlian gums, locust bean gums, gum arabic and gum arabic starches, starch amyloses or alginates are cationically modified, the resultant cationic compounds may also be useful for the compositions of the present invention. Additional examples of suitable compounds are discussed, e.g., in U.S. Pat. No. 6,395,690 to Tsaur, U.S. Pat. No. 5,656,257 to Fealy et al., U.S. Pat. No. 5,900,394 to Goel et al., U.S. Pat. No. 6,083,899 to Baker et al., U.S. Pat. No. 4,438,095 to Grollier et al. and U.S. Pat. No. 6,533,873 to Margiosak et al.

In certain embodiments, the cationic polymeric compound comprises guar. For example, the cationic guar gum resin guar hydroxypropyltrimonium chloride has been found to be particularly useful in certain embodiments, in that compositions containing this compound can maintain a mild and long-lasting cooling, tingling or refreshing effect on the body.

In exemplary embodiments, the amount of cationic polymeric compound present in the compositions is about 0.01 to about 1.0%, in other embodiments about 0.01 to about 0.5%, in other embodiments about 0.05 to about 0.25% and in other embodiments about 0.1 to about 0.2%.

The present embodiments may additionally comprise a solubilizer. As used herein, the term "solubilizer" may refer to any composition that solubilizes at least one of the other ingredients in the composition, and includes, e.g., a fragrance oil, a cosmetic oil, or any composition having an alcohol, including but not limited to: methanol, ethanol, isopropanol, glycerol, ethylene glycol, diethylene glycol, propylene glycol, polypropylene glycol, polyethylene glycol and other polyhydric alcohols. As used herein, the term "solubilizer" also refers to a mixture of any of the foregoing.

The addition of a solubilizer to a composition of two or more sensates has been found to improve even further the ability the composition to maintain the dual benefits of a mild cooling, tingling or refreshing sensation with a long-lasting effect. In certain embodiments, the compositions of the present invention comprise about 0.01 to about 1.0% of a solubilizer. In other embodiments, the compositions comprise about 0.05 to about 0.75% of a solubilizer. In other embodiments, the compositions comprise about 0.10 to about 0.5% of a solubilizer. In still other embodiments, the compositions comprise about 0.15 to about 0.4% of a solubilizer.

Thus, the embodiments are advantageous in that they provide optimal ratios of a first sensate and a second sensate, which, when coupled with a cationic polymeric compound and optionally, a solubilizer, provide mild compositions that are gentle and non-irritating while maintaining a cooling, tingling or refreshing effect to the body of a mammal, including the external skin, scalp and oral cavity of a mammal.

In various embodiments, the present invention is directed to compositions comprising about 0.01 to about 0.3% of a first sensate, about 0.01 to about 0.45% of a second sensate, and about 0.01 to about 1% of a cationic polymeric compound, wherein the ratio of the first sensate to the second sensate is about 1:1 to about 1:2.5, and wherein the compositions provide a cooling, tingling or refreshing sensation when applied to the body. Such compositions have been shown to provide a cooling, tingling or refreshing sensation when applied to the body. In certain embodiments, this sensation remains perceptible after removal of the compositions from contact with the body, e.g., rinsing in the bath or shower, rinsing from the oral cavity, wiping off, spitting out, blotting, or otherwise removing from the oral cavity or skin.

In various embodiments, the present invention is directed to the compositions as described herein in the form of personal care compositions. The personal care compositions may be any acceptable personal care compositions, including but not limited to: hair care products (e.g., shampoos, conditioners, mousses, sprays and hair gels), films, antiperspirants, deodorants, body washes, body gels, body scrubs, creams, lotions, bubble baths, bath powders, bath oils, facial products (e.g., facial cleansers, facial masks, facial scrubs) and other portable forms.

In various embodiments, the present invention is directed to the compositions as described herein in the form of oral care compositions. The oral care compositions may be any acceptable oral care compositions, including but not limited to: dentifrices (such as toothpastes, mouth washes, mouth rinses), mouth or throat sprays, dental adhesives, other oral pastes that are applied to the oral surfaces (e.g., compositions for treating canker sores, cold sores and other mouth sores and lesions, dry mouth or chapped lips), confections (such as, e.g., throat drops, throat lozenges or cough drops) and the like.

The present invention also provides, in certain embodiments, methods for providing to the body a cooling, tingling or refreshing effect comprising applying to the skin a composition comprising about 0.01 to about 0.3% of a first sensate, about 0.01 to about 0.45% of a second sensate and about 0.01 to about 1% of a cationic polymeric compound, wherein the ratio of the first sensate to the second sensate is about 1:1 to about 1:2.5; and removing the compositions provide a cooling, tingling or refreshing sensation that remains perceptible after removal of the composition from contact with the body. In certain embodiments, the invention is directed to the methods as described above, wherein the composition further comprises about 0.01 to about 1% of a solubilizer. In various embodiments, such methods comprise the application of an oral care or personal care composition to the body. In various embodiments, such methods comprise the application a body wash to the skin, and further comprise rinsing the composition from the skin.

As used herein, "applying" includes actions normally associated with oral care and personal care compositions, and includes, e.g., manually rubbing, rubbing with an implement such as a sponge or scrubber, towel, pad, cotton ball or the like, or in the case of an oral care composition, e.g., brushing, dabbing, irrigating, rinsing, spraying, wiping, rubbing, painting, flossing, placement of a film or strip on the surface, implanting and chewing. Conversely, the step of "removing" may refer to, e.g., rinsing, spitting out, removing a film or strip from the surface, swallowing, blow-drying or air drying, or rubbing (as with a towel, sponge or scrubber, washcloth, pad, cotton ball or the like), depending on the specific formulations and intended uses of the compositions of the present invention.

In other embodiments, the present invention provides hair care compositions, as well as methods of providing a cooling, tingling or refreshing effect to the scalp comprising the step of applying a composition comprising a first sensate, a second sensate, a solubilizer and a cationic polymeric compound to the scalp, and removing the composition. The cooling, tingling or refreshing effect may remain on the scalp after the removal of the composition. The composition may be removed in any number of ways, e.g., rinsing, rubbing, blow-drying or air-drying.

In other embodiments, the present invention provides compositions comprising about 0.01 to about 0.3% of a first sensate, about 0.01 to about 0.45% of a second sensate, about 0.01 to about 1.0% propylene glycol and about 0.01 to about 1.0% guar hydroxypropyltrimonium chloride; wherein the ratio of the first sensate to the second sensate is about 1:1 to 1:2.5; wherein the compositions provide a cooling, tingling or refreshing sensation when applied to the body of a mammal, which cooling, tingling or refreshing sensation remains perceptible after removal of the composition from contact with the body of a mammal.

In other embodiments, the present invention provides methods of providing to the skin a cooling, tingling or refreshing feeling comprising the step of applying to the skin an amount of a composition comprising about 0.01 to about 0.3% of a first sensate, about 0.01 to about 0.45% of a second sensate, about 0.01 to about 1.0% propylene glycol and about 0.05 to about 1.0% guar hydroxypropyltrimonium chloride wherein the ratio of the first sensate to the second sensate is about 1:1 to about 1:2.5, and rinsing the composition from the skin. In certain embodiments, the cooling, tingling or refreshing sensation may be maintained after the rinse off step.

In certain embodiments, the invention is directed to compositions of the present invention incorporated into one or more acceptable carriers. Acceptable carriers for the present embodiments may be in liquid, semi-solid or solid phase, and may vary depending upon the composition and intended uses of a particular compound. Additionally, they should be compatible with the compositions themselves and do not degrade or otherwise diminish their efficacy.

Acceptable carriers for the personal care embodiments are dermatologically acceptable and not harsh when applied to the skin, e.g., the skin of the scalp or other areas of the body of a mammal for which personal care compositions are generally intended.

Similarly, acceptable carriers for the oral care embodiments invention should be orally acceptable and not harsh when applied to the teeth or other oral surfaces. In various embodiments, they may be in the form of a mouth rinse, dentifrice, confectionary (including lozenges, drops and gum), medicament, film, or any other form known to one of skill in the art. The carrier optionally comprises, for example, oral care active ingredients, surface active agents, such as surfactants, emulsifiers, and foam modulators, viscosity modifiers and thickeners, humectants, diluents, fillers, additional pH modifying agents, colorants, preservatives, solvents, and combinations thereof. As recognized by one of skill in the art, the oral composition(s) optionally include other materials in addition to those components previously described, including for example, emollients, moisturizers, mouth feel agents and the like. Examples of suitable carriers for oral compositions are disclosed in U.S. Pat. Nos. 6,669,929, 6,379,654, and 4,894,220, the content of each of which are incorporated herein by reference.

Selection of specific carrier components is dependent on the desired product form. It should be understood that any suitable carrier known in the art or to be developed can be provided to the composition, and that the carrier or carriers useful for various embodiments of the present invention will depend upon the specific intended use of the compositions, and that one or more carriers may be suitable for overlapping intended uses.

The compositions of the present invention may also include one or more fragrances. Acceptable fragrances for the present invention include any fragrances that are pleasant and desirable for consumers and do not irritate or otherwise adversely affect the body of a mammal.

In other embodiments, the present invention provides a method of providing a cooling, tingling or refreshing effect to the skin comprising the step of applying a composition to the skin of a mammal comprising a first sensate, a second sensate, a solubilizer and guar hydroxypropyltrimonium chloride. In other embodiments, the present invention provides for a method of providing a cooling, tingling or refreshing effect to the oral cavity comprising the steps of applying a composition to the oral cavity comprising a first sensate, a second sensate, a solubilizer and guar hydroxypropyltimonium chloride, and rinsing the composition from the oral cavity.

In other embodiments, the present invention provides a method of prolonging a cooling, tingling or refreshing sensation to the skin of a mammal, said method comprising the step of applying a composition comprising a first sensate, a second sensate and a cationic polymeric compound to a body of a mammal.

In other embodiments, the present invention provides a method of signaling the delivery of an active agent to the body, comprising the step of applying a composition comprising a first sensate, a second sensate and a cationic polymeric compound to the body of a mammal. As used herein, the term "active agent" refers to any agent that may be applied to the body of a mammal in order to produce a desired physiological effect upon the mammal. Useful active agents for the present invention include, without limitation: emollients, moisturizers, antibacterial agents (e.g., triclosan), humectants, skin toners, sunscreens, skin tanners (e.g., dihydroxyacetone), skin lighteners (e.g., hydroquinone, glycolic acid), vitamins, anti-aging compositions, colorants, pH adjusters, preservatives, pearlescent or opacifying agents, shimmering agents, thickening agents, conditioners, chelating agents/sequestrants, absorbents, abrasives, anticaking agents, astringents, anticaries agents, anti-sensitivity agents (e.g., potassium nitrate), anti-plaque and anti-tartar agents, antifoaming agents, binders, biological additives, buffering agents, bulking agents, chemical additives, cosmetic astringents, denaturants, foam boosters, sugars and starches, sugar and starch derivatives, hydrotropes, neutralizing agents, opacifying agents, plasticizers, propellants, reducing agents, skin protectants or combinations thereof, and similar additives may be included in the compositions described herein and are contemplated by the present invention. In such embodiments, the onset of the cooling, tingling or refreshing effect serves as a signal, thus indicating the delivery of an active agent to the body.

The compositions of the present invention may include these and any ingredients that may further enhance their desirability for consumers, such as, e.g., one or more additional sensates, or any of the foregoing listed potential active agents.

By way of example, and not limitation, specific embodiments of the present invention are illustrated in the following Example.

EXAMPLE

The following materials are mixed together to form a liquid composition that is in accordance with the present invention and that includes optional materials. All percentages are by weight.

| Ingredient | Weight Percentage |
| --- | --- |
| Synthetic Body Wash base (cationic, anionic and nonionic surfactant blend) | 90-96 |
| Menthol | 0.01-0.2 |
| Menthyl Lactate | 0.01-0.4 |
| Propylene Glycol (Solubilizer) | 0.25-1.0 |
| Guar Hydroxypropyltrimonium Chloride | 0.1-0.2 |
| Fragrance | 0.6-1.2 |
| Citric Acid (50% solution) pH adjuster | 0.05-0.5 |
| NaCl (25% solution) viscosity adjuster | q.s. |

The compositions produced as described herein are found by human subjects to exhibit superior tingling, cooling or refreshing effects, coupled with a mild formulation with minimal irritation.

We claim:

1. A composition comprising:
   0.01 to 0.3 weight % of menthol;
   0.01 to 0.45 weight % of menthyl lactate;
   0.01 to 1.0 weight % of guar hydroxypropyltrimonium chloride; and
   0.01 to 1 weight % of propylene glycol;
   wherein the ratio of menthol to menthyl lactate is 1:1 to 1:2.5.

2. The composition of claim 1, wherein the menthol is present in an amount of 0.05 to 0.25 weight %.

3. The composition of claim 1, wherein the menthyl lactate is present in an amount of 0.05 to 0.4 weight %.

4. The composition of claim 1, wherein the guar hydroxypropyltrimonium chloride is present in an amount of 0.01 to 0.5 weight %.

5. The composition of claim 1, wherein the propylene glycol is present in an amount of 0.05 to 0.75 weight %.

6. The composition of claim 1, wherein the propylene glycol is present in an amount of 0.1 to 0.5 weight %.

7. An oral care composition comprising the composition of claim 1 and an acceptable carrier.

8. The composition of claim 7, wherein the oral care composition is a dentifrice.

9. A personal care composition comprising the composition of claim 1 and an acceptable carrier.

10. The personal care composition of claim 9, in the form of a body wash.

11. The personal care composition of claim 9, in the form of a hair care product.

12. A method of providing a cooling, tingling or refreshing sensation to a body of a mammal, said method comprising the step of applying a composition according to claim 1 to a body of a mammal.

13. A method of providing a cooling, tingling or refreshing sensation to the skin, said method comprising the steps of:
   (a) applying to the skin a body wash composition comprising the composition of claim 1, and
   (b) rinsing the composition from the skin.

14. A method of prolonging a cooling, tingling or refreshing sensation to a body, said method comprising the step of applying a composition according to claim 1 to the body.

15. A method of signaling the delivery of an active agent to a body, comprising the step of applying the composition of claim 1, which further comprises an active agent, to the body.

16. The method of claim 15, wherein the active agent is selected from the group consisting of: emollients, moisturizers, antibacterial agents, humectants, skin toners, sunscreens, skin tanners, skin lighteners, vitamins, anti-aging compositions, colorants, pH adjusters, preservatives, pearlescent or opacifying agents, shimmering agents, thickening agents, conditioners, chelating agents/sequestrants, absorbents, abrasives, anticaking agents, astringents, anticaries agents, anti-sensitivity agents, anti-plaque and anti-tartar agents, antifoaming agents, binders, biological additives, buffering agents, bulking agents, chemical additives, cosmetic astringents, denaturants, foam boosters, sugars and starches, sugar and starch derivatives, hydrotropes, neutralizing agents, opacifying agents, plasticizers, propellants, reducing agents, skin protectants or combinations thereof.

17. The composition of claim 1, wherein the ratio of menthol to menthyl lactate is 1:1.5 to 1:2.5.

18. The composition of claim 1, wherein the ratio of menthol to menthyl lactate is 1:2 to 1:2.5.

* * * * *